(12) United States Patent
Kashiki et al.

(10) Patent No.: US 8,742,127 B2
(45) Date of Patent: Jun. 3, 2014

(54) PRODUCTION METHOD OF 6-HALOGENO-3-ARYLPYRIDINE DERIVATIVE

(75) Inventors: Nobusuke Kashiki, Niigata (JP); Toshiki Mori, Ibaraki (JP); Katsuji Ujita, Niigata (JP)

(73) Assignee: Kuraray Co., Ltd. (JP)

( * ) Notice: Subject to any disclaimer, the term of this patent is extended or adjusted under 35 U.S.C. 154(b) by 162 days.

(21) Appl. No.: 12/809,868

(22) PCT Filed: Dec. 19, 2008

(86) PCT No.: PCT/JP2008/073221
§ 371 (c)(1),
(2), (4) Date: Jun. 21, 2010

(87) PCT Pub. No.: WO2009/081872
PCT Pub. Date: Jul. 2, 2009

(65) Prior Publication Data
US 2010/0280253 A1    Nov. 4, 2010

(30) Foreign Application Priority Data

Dec. 21, 2007 (JP) .................................. 2007-330516

(51) Int. Cl.
*C07D 211/72* (2006.01)
(52) U.S. Cl.
USPC ....................................................... 546/345
(58) Field of Classification Search
None
See application file for complete search history.

(56) References Cited

U.S. PATENT DOCUMENTS

| 3,962,268 | A |   | 6/1976  | Lang |           |
|-----------|---|---|---------|------|-----------|
| 4,463,008 | A | * | 7/1984  | Lesher et al. ................. | 514/334 |
| 5,053,521 | A | * | 10/1991 | Pavia ............................ | 548/572 |
| 5,723,621 | A |   | 3/1998  | Shibata et al. | |

FOREIGN PATENT DOCUMENTS

| JP | 50-160279 A   | 12/1975 |
| JP | 09-030989 A   | 2/1997  |
| JP | A-2000-355581 | 12/2000 |
| JP | A-2004-051592 | 2/2004  |
| JP | 2007119379 A  | 5/2007  |
| JP | A-2007-291092 | 11/2007 |

OTHER PUBLICATIONS

Murmann, S.K., J. Amer. Chem. Soc. 1955, vol. 77, pp. 3484-3486.*
Bonnet, V., Synlett., 2002, vol. 67, pp. 1008-1010.*
Parry, P.R. et al., Functionalized Pyridylboronic Acids and Their Suzuki Cross-Coupling Reactions to Yield Novel Heteroarylpyridines, Journal of Organic Chemistry, 2002, vol. 67, No. 21, p. 7541-7543.
Stavenuiter, J. et al., Palladium-Catalyzed Cross-Coupling of Phenylboronic Acid with Heterocyclic Aromatic Halides, Heterocycles, vol. 26, No. 10, 1987, p. 2711-2716.
Yamanaka, H. et al., Sile-Selectivity in the Reaction of 3-Substituted Pyridine 1-Oxides with Phosphorl Chloride, Chem. Pharm. Bull., 1988, vol. 36, p. 2244-2247.
Sekiya, A., et al., The Cross-Coupling of Aryl Halides with Gringnard Reagents Catalyzed by Iodo9Phenyl)Bis (Triphenylphosphine)-Palladium, Journal of Organometallic Chem., 1976, vol. 118, p. 349-354.
Kaczmarek, L., Synthesis and NMR study of new derivatives of [2,2'-bipyridyl]-3,3'-diol and [2,2'-bipyridyl]-3-ol, Journal of Molecular Structure, 2000, vol. 553, p. 61-72.
Bonnet, V., et al., Cross-coupling between 3-Pyridylmagnesium Chlorides and Heteroaromatic Halides, Synlett, 2002, No. 6, p. 1008-1010.
Murmann, R. Kent et al., The Stability of Silver(I) Complexes of Some 3- and 4-Substituted Pyridines, Journal of the American Chemical Society, 1955, vol. 77, No. 13, p. 3484-3486.
Grave, T.B., Attempts to Prepare 1-Methyl-2-Methoxypiperidine. The Hydrogenation of Certain Pyridine Derivatives, Journal of the American Chemical Society, 1924, vol. 46, No. 6, p. 1460-1470.
International Preliminary Report on Patentability issued on PCT/JP2008/73221.
Martin et al., "Pd-catalyzed Kumada-Corriu Cross-Cupling Reactions at Low Temperatures Allow the Use of Knochel-type Grignard Reagents," Journal of American Chemical Society Apr. 4, 2007): vol. 129, No. 13, pp. 3844-3845.
European Search Report for EP Application No. 08863865.5.
Martin et al., "PD-catalyzed Kumada-Corriu Cross-Cupling Reactions at Low Temperatures Allow the Use of Knochel-type Grignard Reagents," Journal of American Chemical Society (Apr. 4, 2007): vol. 129, No. 13, pp. 3844-3845.
European Search Report for EP Application No. 08863865.5, 2012.

* cited by examiner

*Primary Examiner* — Heidi Reese
(74) *Attorney, Agent, or Firm* — Fox Rothschild LLP; Peter J. Butch, III; Robert N. Henrie, II

(57) ABSTRACT

[Problem]
The present invention provides an industrially advantageous production method of a 6-halogeno-3-arylpyridine derivative in which cryogenic condition is not required, production step is short, and an isomer difficult to be separated is not produced as a by-product,
[Solution]
A production method of a 6-halogeno-3-arylpyridine derivative represented by the general formula (III) comprising: the first step reacting a 2,5-dihalogenopyridine derivative represented by the general formula (I) with a magnesiation reagent; and the second step reacting the product obtained from the above-described first step, in the presence of a palladium compound, with a halogenoaryl derivative represented by the general formula (II).

3 Claims, No Drawings

PRODUCTION METHOD OF 6-HALOGENO-3-ARYLPYRIDINE DERIVATIVE

CROSS REFERENCE TO RELATED APPLICATION

The present application is a 35 U.S.C. §371 National Phase application of International Application Serial No. PCT/JP08/73221 filed Dec. 19, 2008, which claims priority under the Paris Convention to Japanese Application Serial No. 2007-330516, filed Dec. 21, 2007. The disclosures of each of these applications are incorporated herein by reference in their entirety.

TECHNICAL FIELD

The present invention, relates to a production method of 6-halogeno-3-arylpyridine derivative, particularly 6-halogeno-3,2'-bipyridine derivative. 6-Halogeno-3-arylpyridine derivative obtained from the present invention is useful as an intermediate for organic synthesis. For example, 6-halogeno-3,2'-bipyridine derivative is useful as the intermediate of therapeutic agent for neurogenic disease (refer to pamphlet of WO2001/96308).

BACKGROUND ART

Heretofore, as the production method of 6-halogeno-3-arylpyridine derivative, (1) a method for reacting 2-halo-5-pyridyl boric acid with arylbromide (see: J. Org. Chem., 2002, vol. 67, page 7541); (2) a method reacting 2-chloro-5-bromopyridine with aryl boric acid (see: Heterocycles 1987, vol. 26, page 2711); (3) a method reacting 1,2,4-triazine prepared by the reaction of 2-chloro-5-cyanopyridine and hydrazine, with 2,5-norbornadiene (see: JP-A-2000-355581); (4) a method for chlorinating 5-arylpyridine (see: Chem. Pharm. Bull., 1988 vol. 36, page 2244) or the like are known.

However, in the method of (1) and (2), cryogenic condition is required in preparing a 2-halo-5-pyridyl boric acid or an aryl boric acid, which are raw material. In addition, in the method of (3), multistep reaction is required. And, in the method of (4), isomers having the different position of chlorination are produced as by-product, therefore, there is a problem that the isomers difficult to separate have been formed. Thus, any methods of the above-described (1) to (4) were not the industrially advantageous methods.

In addition, heretofore, as a cross-coupling process between two aromatic compound derivatives, the method for reacting Grignard compound with halogen compound in the presence of palladium compound is known (see: J. Organometallic Chem., 1976, vol. 118, page 349). However, there are few reaction examples in which arylpyridine derivative is synthesized by reacting Grignard compound of pyridine derivative with halogenoaryl derivative. There is known a method for synthesizing 2-arylpyridine derivative by reacting 2-pyridylmagnesium bromide derivative obtained from the reaction of pyridine derivative which is halogenized at 2-position regarded as generally more reactive substitution site and magnesiation reagent, with halogenoaryl derivative (see: J. Molecular Structure, 2000, Vol. 553, page 61). However, there is not known a method for synthesizing 5-pyridylmagnesiumbromide derivative and halogenoaryl derivative by reacting 5-halogenopyridine derivative having a functional group at 2-position with magnesiation reagent.

DISCLOSURE OF INVENTION

Problem to be Solved by the Invention

It is an object of the present invention to provide an industrially advantageous product ion method of 6-halogeno-3-arylpyridine derivative in which cryogenic condition is not required, production step is short and an isomer difficult to be separated is not produced as a by-product.

Means for Solving the Problem

According to one aspect of the present invention, there is provided a production method of a 6-halogeno-3-arylpyridine derivative (III) including the first step for reacting a 2,5-dihalogenopyridine derivative represented by the following general formula (I) (hereinafter, also called as "2,5-dihalogenopyridine derivative (I)"):

[Formula 1]

(I)

wherein, $X^1$ and $X^2$ independently represents halogen atom, respectively; $R^1$, $R^2$ and $R^3$ independently represents hydrogen atom, optionally substituted alkyl group, optionally substituted cycloalkyl group or optionally substituted aryl group, respectively; $R^1$ and $R^2$ may form optionally substituted cyclic group together with carbon atoms to which they are connected;
with a magnesiation reagent; and the second step reacting the product obtained from the above-described first, step, in the presence of a palladium compound, with a halogenoaryl derivative represented by the following general formula (II) (hereinafter, also called as "halogenoaryl derivative (II)"):

[Formula 2]

(II)

wherein, $X^3$ represents halogen atom; $Y^1$ represents methine group or nitrogen atom; $R^4$ represents hydrogen atom, optionally substituted alkyl group, optionally substituted cycloalkyl group, optionally substituted aryl group, optionally substituted alkoxy group, optionally substituted cycloalkoxy group, or optionally substituted aryloxy group; n represents an integer of 0 to 5;
to obtain a 6-halogeno-3-arylpyridine derivative represented by the following general formula (III) (hereinafter, also called as "6-halogeno-3-arylpyridine derivative (III)"):

[Formula 3]

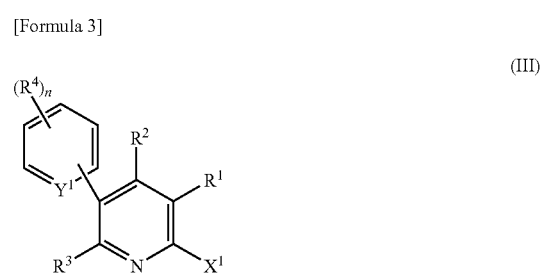

(III)

wherein, $X^1$, $Y^1$, $R^1$, $R^2$, $R^3$, $R^4$ and n are the same as the above-described definition.

In addition, according to another aspect of the present invention, there is provided a production method of a 6-alkoxy-3-arylpyridine derivative (V) including the third step reacting a 6-halogeno-3-arylpyridine derivative (III) with a salt of an alkyl alcohol described in the following general formula (IV):

[Formula 4]

wherein, M represents an element of the first group or the second group in the periodic table; $R^5$ represents an alkyl group or a cycloalkyl group; m is 1 when M is the first group element; m is 2 when M is the second group element; to obtain a 6-alkoxy-3-arylpyridine derivative represented by the following general formula (V) (hereinafter, also called as "6-alkoxy-3-arylpyridine derivative (V)"):

[Formula 5]

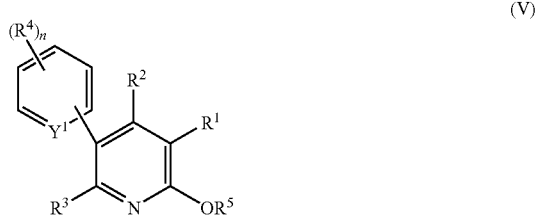

wherein, $Y^1$, $R^1$, $R^2$, $R^3$, $R^4$, $R^5$ and n are the same as the above-described definition.

Advantages of the Invention

According to the present invention, a 6-halogeno-3-arylpyridine derivative (III) can be industrially advantageously produced.

BEST MODE FOR CARRYING OUT THE INVENTION

Production Method of a 6-halogeno-3-arylpyridine Derivative (III)

One aspect of the present invention is the production method of a 6-halogeno-3-arylpyridine derivative (III). This production method is characterized by including the first step for reacting a 2,5-dihalogenopyridine derivative (I) with a magnesiation reagent; and the second step reacting the product obtained from the relevant first step, in the presence of a palladium compound, with a halogenoaryl derivative (II) to obtain a 6-halogeno-3-arylpyridine derivative (III). Therefore, specific aspects other than these ones are not particularly limited. Hereinafter, the preferred embodiment of the production, method of the present aspect is described in detail.

In the above-described general formula, alkyl group represented by each of $R^1$, $R^2$, $R^3$, $R^4$, and $R^5$, and alkyl group contained, in the alkoxy group represented by $R^4$ may be any of the straight chained or branched ones, the preferable carbon atoms thereof are 1 to 12, and 1 to 4 carbon atoms are more preferable. Alkyl group includes, for example, methyl group, ethyl group, propyl group, isopropyl group, n-butyl group, isobutyl group, sec-butyl group, tert-butyl group, hexyl group, octyl group, dodecyl group or the like. Also, cycloalkyl group represented by each of $R^1$ to $R^5$, and cycloalkyl group contained in the cycloalkoxy group represented by $R^4$ are preferably the one having 3 to 12 carbon atoms, and more preferably the one having 5 to 7 carbon atoms. Cycloalkyl group includes cyolopentyl group, cyclohexyl group or the like. In addition, $R^1$ and $R^2$ may form cyclic structure together with carbon atoms of pyridine ring to which they are connected. Carbon atoms of the ring, in which $R^1$ and $R^2$ may form together with them, are preferably 4 to 10. Such a ring includes, for example, benzene ring, naphthalene ring or the like.

The above-described alkyl group, cycloalkyl group, and ring structure may have a substituent. Such substituent includes, for example, aryl group having 4 to 15 carbon atoms, in which hetero atom such as nitrogen atom, oxygen atom, sulfur atom may be arbitrarily contained, such as phenyl group, tolyl group, methoxyphenyl group, nitrophenyl group, naphthyl group, anthracenyl group, pyridyl group, furyl group, thienyl group; alkenyl group such as vinyl group, 1-methylvinyl group; alkoxy group which is the straight chained or branched one having 1 to 12 carbon atoms, such as methoxy group, ethoxy group, propoxy group, isopropoxy group, n-butoxy group, isobutoxy group, tert-butoxy group, hexyloxy group, octyloxy group, dodecyloxy group, allyloxy group, benzyloxy group; cycloalkoxy group having 3 to 12 carbon atoms, such as cyclopentyloxy group, cyclohexyloxy group; aryloxy group having 4 to 15 carbon atoms, in which hetero atom such as nitrogen atom, oxygen atom, sulfur atom may be arbitrarily contained, such as phenoxy group, nitrophenoxy group, naphthyloxy group, anthracenyloxy group, pyridyloxy group, furyloxy group, thienyloxy group.

Optionally substituted alkoxy group represented by $R^4$ is exemplified by methoxy group, ethoxy group, propoxy group, isopropoxy group, n-butoxy group, isobutoxy group, sec-butoxy group, tert-butoxy group, hexyloxy group, octyloxy group, allyloxy group, benzyloxy group or the like. In addition, optionally substituted cycloalkoxy group represented by $R^4$ is exemplified by cyclopentyloxy group, cyclohexyloxy group or the like.

Aryl group represented by each of $R^1$, $R^2$, $R^3$ and $R^4$, as well as aryl group contained in aryloxy group represented by each $R^4$, may arbitrarily contain hetero atom such as nitrogen atom, oxygen atom, and sulfur atom in ring structure and 4 to 15 carbon atoms are preferably contained in this structure. Aryl group includes, for example, phenyl group, naphthyl group, anthracenyl group, pyridyl group, furyl group, thienyl group or the like.

The above-described aryl group may have substituent. Substituent includes, for example, alkyl group, which is the straight chained or branched one having 1 to 12 carbon atoms, such as methyl group, ethyl group, propyl group, isopropyl group, n-butyl group, isobutyl group, sec-butyl group, tert-butyl group, hexyl group, octyl group, dodecyl group; cycloalkoxy group having 3 to 12 carbon atoms such as cyclopentyl group, cyclohexyl group; aryl group having 4 to 15 carbon atoms, in which hetero atom such as nitrogen atom, oxygen atom, sulfur atom may be arbitrarily contained, such as phenyl group, tolyl group, methoxyphenyl group, chlorophenyl group, bromophenyl group, nitrophenyl group, naphthyl group, anthracenyl group, pyridyl group, furyl group, thienyl group; alkoxy group which is the straight chained or branched one having 1 to 12 carbon atoms, such as methoxy group, ethoxy group, propoxy group, isopropoxy group, n-butoxy group, isobutoxy group, sec-butoxy group, tert-butoxy group, hexyloxy group, octyloxy group, dodecyloxy group, allyloxy group, benzyloxy group; cycloalkoxy group having 3 to 12 carbon atoms such as cyclopentyloxy group, cyclohexyloxy group; aryloxy group having 4 to 15 carbon atoms, in which hetero atom such as nitrogen atom, oxygen atom, sulfur atom may be arbitrarily contained, such as phenoxy group, nitrophenoxy group, naphthyloxy group, anthracenyloxy group, pyridyloxy group, furyloxy group, thienyloxy group.

Typical example of aryloxy group represented by $R^4$ includes phenoxy group, nitrophenoxy group, naphthyloxy group, pyridyloxy group, furyloxy group, thienyloxy group or the like.

Element of the first group in the periodic table represented by M in the above-described general formula includes sodium atom, lithium atom, potassium atom or the like. In addition, element of the second group in the periodic table represented by M includes magnesium atom, calcium, atom, or the like.

Production method of the present invention includes the first step for reacting a 2,5-dihalogenopyridine derivative (I) with a magnesiation reagent; and the second step reacting the product obtained from the above-described first step, in the presence of a palladium compound, with a halogenoaryl derivative (II) to obtain a 6-halogeno-3-arylpyridine derivative (III). Hereinafter, each of the steps is described.

[The First Step]

In the first step, a 2,5-dihalogenopyridine derivative (I) is reacted with a magnesiation reagent.

Procuring route of the 2,5-dihalogenopyridine derivative (I) as a reaction material in the first step is not particularly limited. When this is commercially available, one purchased from the relevant commercially available products can be used for the reaction. On the other hand, a 2,5-dihalogenopyridine derivative (I) prepared per se from the industrially available raw material can be used in the first step. Means for preparing per se a 2,5-dihalogenopyridine derivative (I) is exemplified, for example, by the means for substituting methoxy group at 2-position by chlorine, after brominating at 5-position of 2-methoxypyridine (see: Tetrahedron Letters, 1998, vol. 39, page 2059).

As a magnesiation reagent used in the first step, a compound to be used when organic magnesium halide compound is prepared from an organic halogen compound in usual organic chemistry, can be used. For example, magnesium metal; magnesium antracene complex; or a Grignard reagent such as ethylmagnesium bromide, isopropylmagnesium bromide, isopropylmagnesium chloride, t-butylmagnesium chloride is included. Among them, Grignard reagent is preferable from a standpoint of reactivity. Used amount of the magnesiation reagent is preferably in the range of 0.1 to 10 mole equivalent relative to 2,5-dihalogenopyridine derivative (I), more preferably in the range of 0.5 to 3 equivalent.

Reaction is preferably performed in the presence of a solvent. The solvent is not particularly limited as long as it does not have harmful effects to reaction. A solvent includes, for example, aliphatic hydrocarbons such as hexane, heptane, octane; aromatic hydrocarbons such as benzene, toluene, xylene, ethylbenzene, mesitylene; ethers such as tetrahydrofuran, diethyl ether, diisopropyl ether, tert-butylmethyl ether, 1,2-dimethoxyethane, 1,4-dioxane, diethyleneglycol dimethylether. Among them, use of an ether as a solvent is preferable, particularly, use of tetrahydrofuran is preferable from a standpoint of operation of reaction. The solvent can be used alone, or in combination of two or more kinds.

Reaction in the first step is preferably performed in the range of −20 to 100° C., and is more preferably in the range of 0 to 40° C.

Reaction time in the first step is not particularly limited, however usually, is in the range of 0.5 to 24 hours. After completing a reaction, reaction product from the first step may be isolated, and used in the next step, or may be used as reaction mixture as it is in the next step, however, the reaction mixture is preferably used as it is in the next step without further purification. When the reaction mixture from the first step is isolated, method in which the reaction mixture is left to stand and is filtered to obtain the reaction products precipitated as solid; or method in which the reaction mixture is condensed by distilling off the solvent, can be used as an isolating method.

In the first step, it is estimated that an organic magnesium compound represented by the following general formula (VI) (hereinafter, also called as "organic magnesium compound (VI)") is formed by reacting a 2,5-dihalogenopyridine derivative (I) with a magnesiation reagent. In the second step to be described later, it is understood that coupling reaction of an organic magnesium compound (VI) and a halogenoaryl derivative (II), is performed. However, technical scope of the present invention is not limited by this reaction mechanism

[Formula 6]

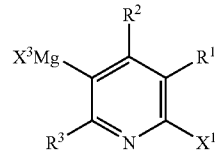

(VI)

wherein, $X^3$ represents halogen atom, $X^1$, $R^1$, $R^2$ and $R^3$ are as the above-described definitions.

[The Second Step]

In the second step, the above-described product from the first step (estimated as organic magnesium compound (VI)) is, in the presence of a palladium compound, reacted with a halogenoaryl derivative (II). By this reaction, a 6-halogeno-3-arylpyridine derivative (III) is obtained.

Procuring route of the halogenoaryl derivative (II) as a reaction raw material in the second step is not particularly limited. When this is commercially available, one purchased from the relevant commercially available products can be used for the reaction. On the other hand, a halogenoaryl derivative (II) prepared per se from the industrially available raw material, can be used in the second step. Means for preparing per se a halogenoaryl derivative (II), is exemplified, for example, by the means of substituting amino group of 2-aminopyridine with bromine (see: Organic Synthesis, Collective Vol. 3, page 136, 1955).

Used amount, of the halogenoaryl derivative (II) is preferably in the range of 0.1 to 10 mole relative to 1 mole of the 2,5-dihalogenopyridine derivative (I) used in the first, step, more preferably in the range of 0.3 to 2 mole equivalent.

Reaction of the second step is preferably performed in the range of −20 to 100° C., more preferably in the range of 0 to 40° C.

Palladium compound to be used in the second step is not particularly limited as long as it is generally used for the reaction of carbon-carbon bond formation. The palladium compound includes, for example, tetrakis(triphenylphosphine)palladium(0), bis[1,2-bis(diphenylphosphino)ethane]palladium(0), bis[1,3-bis(diphenylphosphino)propane]palladium(0), bis[1,4-bis(diphenylphosphino)butane]palladium(0), bis[1,5-bis(diphenylphosphino)pentane]palladium(0), bis[1,6-bis(diphenylphosphino)hexane]palladium(0), bis[1,1'-bis(diphenylphosphino)ferrocene]palladium(0), palladium(0), tris(dibenzylideneacetone)dipalladium(0), bis(tri-t-butylphosphine)palladium(0), bis(tricyclohexylphosphine)palladium(0), palladium(II) chloride, palladium(II) acetate, dichlorobis(triphenylphosphine)palladium(II), dichlorobis[methylenebis(diphenylphosphine)]dipalladium, [1,2-bis(diphenylphosphino)ethane]dichloropalladium(II), [1,3-bis(diphenylphosphino)propane]dichloropalladium(II), [1,4-bis(diphenylphosphino)butane]dichloropalladium(II), [1,5-bis(diphenylphosphino)pentane]dichloropalladium(II), [1,6-bis(diphenylphosphino)hexane]dichloropalladium(II), [1,1'-bis(diphenylphosphino)ferrocene]dichloropalladium(II), palladium(II) acetylacetonate, bis(benzonitrile)palladium(II) chloride, bis(acetate)bis(triphenylphosphine)palladium(II), bis(acetonitrile) dichloropalladium(II), bis(benzonitrile) dichloropalladium(II) or the like. From the standpoint of stability, reactivity, ease of procurement, among them, tetrakis(triphenylphosphine)palladium(0), bis[1,2-bis(diphenylphosphino)ethane]palladium(0), bis[1,3-bis(diphenylphosphino)propane]palladium(0), bis[1,4-bis(diphenylphosphino)butane]palladium(0), bis[1,5-bis(diphenylphosphino)pentane]palladium(0), bis[1,6-bis(diphenylphosphino)hexane]palladium(0), bis[1,1'-bis(diphenylphosphino)ferrocene]palladium(0), bis(tri-t-butylphosphine)palladium(0), bis(tricyclohexylphosphine)palladium(0), dichlorobis(triphenylphosphine)palladium(II), dichlorobis[methylenebis(diphenylphosphine)]dipalladium, [1,2-bis(diphenylphosphino)ethane]dichloropalladium(II), [1,3-bis(diphenylphosphino)propane]dichloropalladium(II), [1,4-bis(diphenylphosphino)butane]dichloropalladium(II), [1,5-bis(diphenylphosphino)pentane]dichloropalladium(II), [1,6-bis(diphenylphosphino)hexane]dichloropalladium(II), [1'-bis(diphenylphosphino)ferrocene]dichloropalladium(II), bis(acetate)bis(triphenylphosphine)palladium(II), bis(acetonitrile)dichloropalladium(II) or the like is preferable, palladium complex compound having bidentate phosphorus ligand such as dichlorobis[methylenebis(diphenylphosphine)]dipalladium, [1,2-bis(diphenylphosphino)ethane]dichloropalladium(II), [1,3-bis(diphenylphosphino)propane]dichloropalladium(II), [1,4-bis(diphenylphosphino)butane]dichloropalladium(II), [1,5-bis(diphenylphosphino)pentane]dichloropalladium(II), [1,6-bis(diphenylphosphino)hexane]dichloropalladium(II), [1,1'-bis(diphenylphosphino)ferrocene]dichloropalladium(II) is more preferable, and [1,1'-bis(diphenylphosphino) ferrocene]dichloropalladium(II) is further preferable. Palladium compound to be used in the second step may be the commercially available one, or the one produced during reaction system.

If necessary, a phosphorus ligand, which can be coordinated to the above-described palladium compound, may be used appropriately. The phosphorus ligand to be used includes, for example, triphenylphosphine, tri-o-tolylphosphine, tri-m-tolylphosphine, tri-p-tolylphosphine, tris(2,6-dimethoxyphenyl)phosphine, tris[2-(diphenylphosphino)ethyl]phosphine, bis(2-methoxyphenyl)phenylphosphine, 2-(di-t-butylphosphino)biphenyl, 2-(dicyclohexylphosphino)biphenyl, 2-(diphenylphosphino)-2'-(N,N-dimethylamino)biphenyl, tri-t-butylphosphine, bis(diphenylphosphino)methane, 1,2-bis(diphenylphosphino)ethane, 1,2-bis(dimethylphosphino)ethane, 1,3-bis(diphenylphosphino)propane, 1,4-bis(diphenylphosphino)butane, 1,5-bis(diphenylphosphino)pentane, 1,6-bis(diphenylphosphino)hexane, 1,2-bis(dimethyiphosphino)ethane, 1,1'-bis(diphenylphosphino)ferrocene, bis(2-diphenylphosphinoethyl)phenylphosphine, bis(2-diphenylphosphinophenyl)ether or the like. Suitably, bidentate phosphorus ligand such as bis(diphenylphosphino)methane, 1,2-bis(diphenylphosphino)ethane, 1,2-bis(dimethyiphosphino)ethane, 1,3-bis(diphenylphosphino)propane, 1,4-bis(diphenylphosphino)butane, 1,5-bis(diphenylphosphino)pentane, 1,6-bis(diphenylphosphino)hexane, 1,2-bis(dimethyiphosphino)ethane, 1,1'-bis(diphenylphosphino)ferrocene, bis(2-diphenylphosphinoethyl)phenylphosphine is preferable, 1,1'-bis(diphenylphosphino)ferrocene is more preferable.

Used amount of the palladium compound is preferably in the range of 0.0001 to 2 equivalents relative to the one of halogenoaryl derivative (II), more preferably in the range of 0.001 to 0.1 equivalents.

As the operation of reaction, a halogenoaryl derivative (II) and a palladium compound are added to the reaction mixture containing the reaction product from the first step, or the reaction mixture containing the reaction product from the first step are added to a solution of a halogenoaryl derivative (II) and a palladium compound. When adding, the halogenoaryl derivative (II) may be diluted by the above-described reaction solvent. Diluted concentration is not particularly limited, however, is preferably in the range of 1 to 80% by weight, more preferably in the range of 5 to 50% by weight. Addition rate is not particularly limited, however, the rate controllable the temperature, at which preferable reaction performance can be expressed, is preferable.

Reaction time is not particularly limited, however, is usually in the range of 0.5 to 24 hours. The 6-halogeno-3-arylpyridine derivative (III) produced in this way can be isolated and purified by the usual method to be used for isolation/purification of organic compound. For example, the reaction mixture is neutralized by hydrochloric acid or the like, and is extracted with an organic solvent such as toluene, then treated by distillation, silica gel column chromatography, recrystallization to purify the objective 6-halogeno-3-arylpyridine derivative (III).

Production Method of a 6-alkoxy-3-arylpyridine Derivative (V)

Another aspect of the present invention is the production method of a 6-alkoxy-3-arylpyridine derivative (V). This production method is characterized by a point including the third step in which a 6-alkoxy-3-arylpyridine derivative (V) is obtained by reacting a 6-halogeno-3-arylpyridine derivative (III) with a salt of alkyl alcohol (IV). Therefore, specific aspect other than the method is not particularly limited. Hereinafter, preferable embodiment of the production method of the present aspect is described in detail.

[The Third Step]

In the third step, a 6-halogeno-3-arylpyridine derivative (III) is reacted with a salt of alkyl alcohol (IV) to obtain a 6-alkoxy-3-arylpyridine derivative (V). It should be noted that, procuring route of the 6-halogeno-3-arylpyridine derivative (III) as a raw material of the reaction in the third step is not particularly limited. For example, it may be the one obtained via the above-described first step and second step, or may be the one produced by the other general means by oneself, and may be the one purchased from the commercially available products.

Used amount of the salt of the alkyl alcohol (IV) is preferably in the range of 0.1 to 10 moles relative to 1 mole of the 6-halogeno-3-arylpyridine derivative (III), more preferably in the range of 0.5 to 3 moles.

Reaction is preferably performed in the presence of a solvent. The solvent is not particularly limited, as long as it does not have harmful effects to reaction. The solvent includes, for example, aliphatic hydrocarbons such as hexane, heptane, octane; aromatic hydrocarbons such as benzene, toluene, xylene, ethylbenzene, mesitylene; ethers such as tetrahydrofuran, diethyl ether, diisopropyl ether, tert-butylmethyl ether, 1,2-dimethoxyethane, 1,4-dioxane, diethyleneglycol dimethylether. Among them, use of an aromatic hydrocarbon is preferable, From the standpoint of operation of reaction, use of toluene is particularly preferable. A solvent may be used alone, or in combination of two or more kinds.

Reaction in the third step is preferably performed in the range of 0 to 200° C., more preferably in the range of 60 to 100° C.

Reaction time in the third step is not particularly limited, however usually, is in the range of 0.5 to 24 hours.

The 6-alkoxy-3-arylpyridine derivative (V) produced by such a process can be isolated and purified by the usual method to be used for the isolation/purification of organic compound. For example, the reaction mixture is neutralized by hydrochloric acid or the like, and extracted with an organic solvent, such as toluene, then treated by distillation, silica gel column chromatography, recrystallization to purify the objective 6-alkoxy-3-arylpyridine derivative (V).

EXAMPLES

Hereinafter, the present invention is specifically described by the examples, however, the present invention is by no means limited by these examples. It should be noted that, in the following examples, comparative examples, referential examples, as for the palladium compound and isopropylmagnesium chloride, reagent produced by Tokyo Chemical Industry Co., Ltd. were used, and as for other raw material compounds other than them and solvents, reagent produced by Wako Pure Chemical Industries, Ltd. were used.

Example 1

Synthesis of 6-chloro-3-phenylpyridine

In a 300 mL inner volume flask replaced by nitrogen, 30.3 g of tetrahydrofuran solution containing 19.5% by weight of isopropylmagnesium chloride (57.5 mmol as isopropylmagnesium chloride) as a magnesiation reagent was charged, and cooled at 10° C., and then 20 g of tetrahydrofuran solution containing 5-bromo-2-chloropyridine (9.6 g, 50.0 mmol) as a 2,5-dihalogenopyridine derivative (I), was added dropwise in the range of 10 to 20° C. for 1.0 hour. After adding dropwise, the reaction mixture was stirred in the range of 10 to 20° C. for 1.5 hours, and then added dropwise to the solution of tetrahydrofuran (20 g) containing bromobenzene (7.9 g, 50.0 mmol) as a halogenoaryl derivative (II), and [1,1'-bis(diphenylphosphino)ferrocene]dichloropalladium(II) (0.20 g, 0.25 mmol) as a palladium compound in the range of 10 to 20° C. for 2.0 hours. After adding dropwise, the reaction mixture was stirred in the range of 10 to 20° C. for 4.0 hours, and then saturated aqueous solution of ammonium chloride (50 g) was added. Toluene (50 g) was added to the reaction mixture, and after stirring for 1.0 hour, the reaction mixture was left to stand to separate the organic layer. After washing the organic layer with saturated sodium chloride solution (10 g), it was condensed under reduced pressure to obtain crude 6-chloro-3-phenylpyridine (6.5 g, purity: 82%, yield: 60%). The resultant crude 6-chloro-3-phenylpyridine (6.5 g) was purified by silica gel column chromatography (200 g), and 6-chloro-3-phenylpyridine (4.5 g, yield: 42%) as a 6-halogeno-3-arylpyridine derivative (III) was obtained.

$^1$H-NMR spectrum (300 MHz, CDCl$_3$, TMS, ppm) δ: 7.37-7.58 (m, 6H), 7.84 (dd, 1H, J=8.3, 2.5 Hz), 8.61 (d, 1H, 2.0 Hz).

Example 2

Synthesis of 6-chloro-3-phenylpyridine

The same operation as example 1 was carried out except chlorobenzene (5.6 g, 50.0 mmol) was used instead of bromobenzene, to obtain 6-chloro-3-phenylpyridine as 40% of yield.

Example 3

Synthesis of 6-chloro-3,2'-bipyridine

In a 300 mL inner volume flask replaced by nitrogen, tetrahydrofuran solution of isopropylmagnesium chloride (19.5% by weight, 30.3 g, 57.5 mmol) as a magnesiation reagent was charged, and cooled at 10° C., then tetrahydrofuran solution (20 g) of 5-bromo-2-chloropyridine (9.6 g, 50.0 mmol) as a 2,5-dihalogenopyridine derivative (I) was added dropwise in the range of 10 to 20° C. for 1.0 hour. After adding dropwise, the reaction mixture was stirred in the range of 10 to 20° C. for 1.5 hours, then the reaction mixture was added dropwise to the solution of tetrahydrofuran (20 g) containing 2-bromopyridine (7.9 g, 50.0 mmol) as a halogenoaryl derivative (II) and [1,1'-bis(diphenylphosphino)ferrocene]dichloropalladium(II) (0.20 g, 0.25 mmol) as a palladium compound, in the range of 10 to 20° C. for 2.0 hours. After adding dropwise, the reaction mixture was stirred in the range of 10 to 20° C. for 4.0 hours, then reaction was stopped by adding saturated aqueous solution of ammonium chloride (50 g), and was left to stand to isolate organic layer. Organic layer was washed with saturated sodium chloride solution (10 g), then condensed under reduced pressure, to obtain crude 6-chloro-3,2'-bipyridine (10.6 g, purity: 81%, yield: 90%). The resultant crude 6-chloro-3,2'-bipyridine (10.6 g) was subjected to simple distillation under reduced pressure (0.9 mmHg, 124° C.), to obtain 6-chloro-3,2'-bipyridine (8.0 g, yield: 68%) as a 6-halogeno-3-arylpyridine derivative (III).

$^1$H-NMR spectrum (300 MHz, CDCl$_3$, TMS, ppm) δ: 7.27-7.33 (m, 1H), 7.42 (d, 1H, J=7.5 Hz), 7.72 (d, 1H, J=7.9 Hz), 7.77-7.82 (m, 1H), 8.25 (dd, 1H, J=2.0 Hz, 7.8 Hz), 8.68-8.72 (m, 1H, J=Hz), 8.96 (d, 1H, J=2.0 Hz).

Examples 4 to 9

The same operation as example 3 was carried out except the compound described in Table 1 below was used as the halogenoaryl derivative (II) and the palladium compound. Product and yield thereof were shown in Table 1 together.

TABLE 1

|  | Halogenoaryl derivative (II) | Palladium compound | yield (%) |
|---|---|---|---|
| Example 3 | 2-brompyridine | Pd(dppf)Cl$_2$ | 90 |
| Example 4 | 2-bromopyridine | Pd(PPh$_3$)$_4$ | 50 |
| Example 5 | 2-bromopyridine | Pd(dppe)Cl$_2$ | 50 |
| Example 6 | 2-bromopyridine | Pd(dppp)Cl$_2$ | 60 |
| Example 7 | 2-bromopyridine | Pd(dppb)Cl$_2$ | 75 |
| Example 8 | 2-chloropyridine | Pd(dppe)Cl$_2$ | 40 |
| Example 9 | 2-chloropyridine | Pd(dppf)Cl$_2$ | 60 |

Pd(PPh$_3$)$_4$: tetrakis (triphenylphosphine) palladium (0);
Pd(dppe)Cl$_2$: [1,2-bis(diphenylphosphino)ethane]dichloropalladium(II);
Pd(dppp)Cl$_2$: [1,3-bis(diphenylphosphino)propane]dichloropalladium(II);
Pd(dppb)Cl$_2$: [1,4-bis(diphenylphosphino)butane]dichloropalladium(II);
Pd(dppf)Cl$_2$: [1,1'-bis(diphenylphosphino)ferrocene]-dichloropalladium(II)

Example 10

Synthesis of 6-methoxy-3,2'-bipyridine

In a 200 mL inner volume flask, toluene solution (10 g) containing 6-chloro-3,2'-bipyridine (6.0 g, 31.5 mmol) of 6-halogeno-3-arylpyridine derivative (III) was charged, and methanol solution containing sodium methoxide (32.0% weight, 8.0 g, 47.4 mmol) of salt of alkyl alcohol (IV) was added dropwise in the range of 10 to 20° C. for 0.5 hour. After adding dropwise, the reaction mixture was stirred in the range of 70 to 75° C. for 3.0 hours, and then reaction was stopped by adding water (30 g) in the range of 10 to 20° C. Toluene (20 g) was added to the reaction mixture, and stirred for 1.0 hour, then left to stand to isolate organic layer. Aqueous layer was extracted with toluene (30 g+30 g) two times, and the extract and the above-described organic layer were combined, and then condensed under reduced pressure to obtain crude 6-methoxy-3,2'-bipyridine (6.2 g, purity: 91%, yield: 95%). The resultant crude 6-methoxy-3,2'-bipyridine (6.2 g) was distilled simply (1.0 mmHg, 104° C.) to obtain 6-methoxy-3,2'-bibipyridine (5.4 g, yield: 83%) as a 6-alkoxy-3-arylpyridine derivative (V).

$^1$H-NMR spectrum (300 MHz, CDCl$_3$, TMS, ppm) δ: 4.00 (s, 3H), 6.85 (d, 1H, J=8.9 Hz), 7.20-7.24 (m, 1H), 7.66 (d, 1H, J=7.9 Hz), 7.74 (dt, 1H, J=2.0 Hz, 7.9 Hz), 8.25 (dd, 1H, J=2.0 Hz, 8.9 Hz), 8.66-8.68 (m, 1H,), 8.74 (d, 1H, J=2.0 Hz).

Comparative Example 1

Synthesis of 6-chloro-3,2'-bipyridine in the Presence of Nickel Compound

In a 300 mL inner volume flask replaced by nitrogen, tetrahydrofuran solution containing isopropylmagnesium chloride (19.5% by weight, 30.3 g, 57.5 mmol) was charged, and cooled at 10° C., and then, tetrahydrofuran solution (20 g) containing 5-bromo-2-chloropyridine (9.6 g, 50.0 mmol) was added dropwise in the range of 10 to 20° C. for 1.0 hour. After adding dropwise, the reaction mixture was stirred in the range of 10 to 20° C. for 1.5 hours, and then reaction mixture was added dropwise to the solution of tetrahydrofuran (20 g) containing 2-bromopyridine (7.9 g, 50.0 mmol) and [1,1'-bis(diphenylphosphino)propane]nickel dichloride (0.14 g, 0.25 mmol) in the range of 10 to 20° C. for 2.0 hours. After adding dropwise, the reaction mixture was stirred in the range of 10 to 20° C. for 4.0 hours. However, 6-chloro-3,2'-bipyridine could not be obtained.

Referential Example 1

Synthesis of 6-chloro-3,2'-bipyridine by Suzuki Coupling (−78° C.)

In a flask replaced by nitrogen, tetrahydrofuran solution (80 g) containing 5-bromo-2-chloropyridine (9.6 g, 50.0 mmol) was charged, and cooled at −78° C., and then n-hexane solution of n-butyllithium (15% by weight, 24.6 g, 57.5 mmol) was added dropwise at −78° C. Next, at −78° C., trimethoxyborane (5.7 g, 55.0 mmol) was added dropwise. After 30 minutes from adding dropwise, cooling bath was removed off, and the reaction mixture was stirred at room temperature overnight. Then, 10% by weight of hydrochloric acid (50 g) was added under ice cooling condition, and the reaction mixture was stirred for 1.5 hours, and then neutralized by adding 40% by weight of sodium hydroxide aqueous solution (15 g). Ethyl acetate (50 g) was added to the reaction mixture, and the reaction mixture was stirred for 1.0 hour, and then left to stand to separate organic layer. Organic layer was dried with anhydrous magnesium sulfate, and then condensed under reduced pressure to obtain 6-chloro-3-pyridylboronic acid (6.9 g, 44.0 mmol).

2-bromopyridine (7.0 g, 44.0 mmol), palladium acetate (0.5 g, 2.2 mmol), triphenylphosphine (2.5 g, 9.5 mmol), potassium carbonate (37.0 g, 267.0 mmol), 1,2-dimethoxyethane (60 g) and water (80 g) were added to the resultant 6-chloro-3-pyridyl boronic acid (6.9 g, 44.0 mmol), and the reaction mixture was stirred, and then refluxed with heating for 6.0 hours. Reaction solution was cooled, and then ethyl acetate (50 g) was added, the reaction solution was stirred for 1.0 hour, and was left to stand to separate organic layer. Organic layer was washed with 10% by weight of aqueous solution of ammonium chloride (20 g), 10% aqueous solution of ammonia (20 g), 10% aqueous solution of sodium chloride (20 g), and then condensed under reduced pressure to obtain 6-chloro-3,2'-bipyridine (7.0 g, 38.3 mmol).

Referential Example 2

Synthesis of 6-chloro-3,2'-bipyridine by Suzuki Coupling (10° C.)

In a flask replaced by nitrogen, tetrahydrofuran solution (80 g) of 5-bromo-2-chloropyridine (9.6 g, 50.0 mmol) was charged, and cooled at 10° C., and then n-hexane solution of n-butyllithium (15% by weight, 24.6 g, 57.5 mmol) was added dropwise at 10° C. Next, at 10° C., trimethoxyborane (5.7 g, 55.0 mmol) was added dropwise. After 30 minutes from adding dropwise, cooling bath was removed off, and the reaction mixture was stirred at room temperature overnight. However, 6-chloro-3-pyridylboronic acid could not be obtained.

Comparative Example 2

Synthesis of 6-methoxy-3,2'-bipyridine

In a 300 mL inner volume flask replaced by nitrogen, tetrahydrofuran solution of isopropylmagnesium chloride (19.5% by weight, 30.3 g, 57.5 mmol) was charged, and cooled at 10° C., and then tetrahydrofuran solution (20 g) of 5-bromo-2-methoxypyridine (9.4 g, 50.0 mmol) was added dropwise in the range of 10 to 20° C. for 1.0 hour. After adding dropwise, the reaction mixture was stirred in the range of 10 to 20° C. for 1.5 hours, and then added dropwise to the tetrahydrofuran solution (20 g) containing 2-bromopyridine (7.9 g, 50.0 mmol) and [1,1'-bis(diphenylphosphino)ferrocene]dichloropalladium(II) (0.14 g, 0.25 mmol) in the range of 10 to 20° C. for 2.0 hours. After adding dropwise, the reaction mixture was stirred in the range of 10 to 20° C. for 4.0 hours, however, 6-methoxy-3,2'-bipyridine could not be obtained.

It should be noted that the present patent application was based on Japanese Patent Application Number 2007-330516 filed on Dec. 21, 2007, and the disclosure is incorporated by reference in its entirety.

The invention claimed is:

1. A method for synthesizing a 6-halo-3-aryl-pyridine compound comprising:
   reacting a 2,5-dihalopyridine derivative represented by the following general formula (I):

[Formula 1]

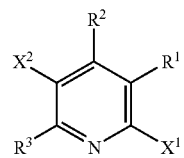
   (I)

wherein, $X^1$ represents a chloro atom and $X^2$ represents a bromo atom; $R^1$, $R^2$ and $R^3$ each represent a substituent independently selected from the group consisting of a hydrogen atom, an optionally substituted alkyl group, an optionally substituted cycloalkyl group and an optionally substituted aryl group; provided that in the alternative $R^1$ and $R^2$ may also be selected to form an optionally substituted ring together with the carbon atoms to which they are connected, with a magnesiation reagent to form the product of a magnesiation reaction comprising a 2-halo-5-pyridyl magnesium species; and reacting the magnesiation reaction product in the presence of a palladium compound, with a halogenoaryl derivative represented by the following general formula (II):

[Formula 2]

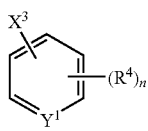

(II)

wherein, $X^3$ represents a halogen atom; $Y^1$ represents a CH group or nitrogen atom; each $R^4$ represents a substituent independently selected from the group consisting of a hydrogen atom, an optionally substituted alkyl group, an optionally substituted cycloalkyl group, an optionally substituted aryl group, an optionally substituted alkoxy group, an optionally substituted cycloalkoxy group and an optionally substituted aryloxy group; and n represents an integer of 0 to 5;

to obtain a 6-halo-3-arylpyridine derivative represented by the following general formula (III):

[Formula 3]

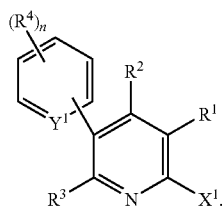

(III)

2. The method of claim 1, wherein $Y^1$ represents nitrogen atom.

3. The method of claim 1, further comprising the step of:

reacting the 6-halo-3-arylpyridine derivative represented by the general formula (III) with a salt of an alkyl alcohol represented by the following general formula (IV):

[Formula 4]

$$M(OR^5)_m \qquad (IV)$$

wherein, M represents an element of the first group or the second group in the periodic table; $R^5$ represents an alkyl group or a cycloalkyl group; and m is 1 when M is the first group element or m is 2 when M is the second group element;

to obtain a 6-alkoxy-3-arylpyridine derivative represented by the general formula (V):

[Formula 5]

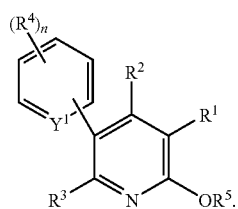

(V)

* * * * *